United States Patent
Pan et al.

(10) Patent No.: US 9,359,386 B1
(45) Date of Patent: Jun. 7, 2016

(54) SILANES AND SILICONES WITH DISTINCT HYDROPHILIC AND OLEOPHOBIC SUBSTITUTION

(71) Applicant: Gelest Technologies, Inc., Morrisville, PA (US)

(72) Inventors: Youlin Pan, Langhorne, PA (US); Barry C. Arkles, Pipersville, PA (US)

(73) Assignee: Gelest Technologies, Inc., Morrisville, PA (US)

( * ) Notice: Subject to any disclaimer, the term of this patent is extended or adjusted under 35 U.S.C. 154(b) by 0 days.

(21) Appl. No.: 15/017,946

(22) Filed: Feb. 8, 2016

Related U.S. Application Data

(60) Provisional application No. 62/118,180, filed on Feb. 19, 2015.

(51) Int. Cl.
*C07F 7/12* (2006.01)
*C07F 7/18* (2006.01)

(52) U.S. Cl.
CPC .. *C07F 7/12* (2013.01); *C07F 7/184* (2013.01)

(58) Field of Classification Search
CPC .................................. C07F 7/12; C07F 7/184
USPC .......................................... 556/445, 487, 488
See application file for complete search history.

(56) References Cited

U.S. PATENT DOCUMENTS

| | | | | |
|---|---|---|---|---|
| 7,928,179 B2 * | 4/2011 | Yoshikawa | ............. | C08G 77/14 428/447 |
| 8,962,138 B2 * | 2/2015 | Bauer | .................... | C08G 77/04 428/402 |
| 2003/0198869 A1 | 10/2003 | West et al. | | |
| 2013/0280485 A1 | 10/2013 | Coclite et al. | | |

OTHER PUBLICATIONS

Arkles, B. et al. "The Role of Polarity on the Substitution of Silanes Employed in Surface Modification." Silanes and Other Coupling Agents, vol. 5, K. Mittal Ed. p. 51 VSP (Brill) 2009.

* cited by examiner

*Primary Examiner* — Porfirio Nazario Gonzalez
(74) *Attorney, Agent, or Firm* — Panitch Schwarze Belisario & Nadel LLP

(57) ABSTRACT

The invention relates to silicon compounds having formula (I):

$$(R_fCH_2CH_2)_{2-n}[R(OCH_2CHR')_mOR'']_nSiX_2 \qquad (I).$$

In formula (I), Rf is a linear or branched perfluorinated hydrocarbon having 4 or more carbon atoms, R is a methyl or ethyl group, R' is H or $CH_3$, m is an integer of 1 to about 24, R" is a hydrocarbon bridge having 1 to about 11 carbon atoms, n is an integer from 0 to 2, and X is H, Cl or an alkoxy group. The inventive materials may be used to produce siloxanes or silicones by hydrolytic condensation and have utility in surface modification.

21 Claims, No Drawings

SILANES AND SILICONES WITH DISTINCT HYDROPHILIC AND OLEOPHOBIC SUBSTITUTION

CROSS REFERENCE TO RELATED APPLICATION

This application claims priority to U.S. Provisional Patent Application No. 62/118,180, filed Feb. 19, 2015, the disclosure of which is herein incorporated by reference.

BACKGROUND OF THE INVENTION

Exposure of transparent functional surfaces, particularly those associated with integrated displays and medical devices, to bioburden and environmental contamination present both functional and hygienic challenges which can interfere with device performance or cause device failure. As a consequence, there has been an accelerating interest in coatings that purport to be self-cleaning. These coatings are sometimes referred to as super-amphiphobic or super-omniphobic. Anti-fogging and anti-icing coatings are often associated with the same concepts. While control of physical topography and fabrication techniques are essential elements in achieving coating performance, nearly all of the proposed coatings utilize building blocks that contain components with extremely low polarity for oleophobicity, such as perfluorinated hydrocarbons, or with aprotic high polarity, such as polyethers for hydrophilicity. Silanes and silicones are often of interest as building blocks for these coatings due to their ability to form thin films.

To date, there are few examples of silanes and silicones that contain distinct low polarity and high polarity substitutions on a single silicon atom, but 1,1,2,2-tetrahydroperfluoroalkylsilanes and polyethyleneoxysilanes are well known. More limited are examples in which high polarity and low polarity blocks are combined in a single substitution, such as dodecyloxypolyethyleneoxypropyl silanes. In order to control the structure of coatings on a nanostructural level, it is highly desirable to provide silanes, both as surface treatments and as silicone monomers, in which substitutions on the silicon atom have independent low polarity and high polarity. By independently controlling oleophobicity and hydrophilicity at a molecular level, the opportunity is afforded to structure surfaces which are less susceptible to the formation of adherent films derived from environmental or biological contamination. Further, polymeric siloxanes derived from these materials are potentially surfactants.

SUMMARY OF THE INVENTION

In one embodiment, the invention relates to a silicon compound having formula (I):

(RfCH$_2$CH$_2$)$_{2-n}$[R(OCH$_2$CHR')$_m$OR'']$_n$SiX$_2$     (I)

wherein Rf is a linear or branched perfluorinated hydrocarbon having 4 or more carbon atoms, R is a methyl or ethyl group, R' is H or CH$_3$, m is an integer of 1 to about 24, R'' is a hydrocarbon bridge having 1 to about 11 carbon atoms, n is an integer from 0 to 2, and X is H, Cl or an alkoxy group.

The invention also includes a [(methoxypolyethyleneoxy)alkyl]hydridodichlorosilane.

In a further embodiment, the invention relates to a siloxane polymer having formula (II):

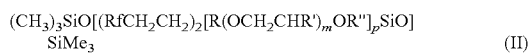
(CH$_3$)$_3$SiO[(RfCH$_2$CH$_2$)$_2$[R(OCH$_2$CHR')$_m$OR'']$_p$SiO]SiMe$_3$     (II)

wherein Rf is a linear or branched perfluorinated hydrocarbon having 4 or more carbon atoms, R is a methyl or ethyl group, R' is H or CH$_3$, m is an integer of 1 to about 24, R'' is a hydrocarbon bridge having 1 to about 11 carbon atoms, and p is an integer from 0 to 100.

DETAILED DESCRIPTION OF THE INVENTION

The present invention relates to a series of new silicon compounds having formula (I):

(RfCH$_2$CH$_2$)$_{2-n}$[R(OCH$_2$CHR')$_m$OR'']$_n$SiX$_2$     (I)

In formula (I), Rf is a linear or branched perfluorinated hydrocarbon having 4 or more carbon atoms (preferably 4 to about 10), R is a methyl or ethyl group, R' is H or CH$_3$, m is an integer of 1 to about 24, preferably about 2 to 6, R'' is a hydrocarbon bridge having 1 to about 11 carbon atoms, preferably CH$_2$CH$_2$CH$_2$, n is an integer from 0 to 2 and X is H, Cl or an alkoxy group, preferably methoxy or ethoxy. Thus, in a preferred embodiment of the invention (n=1), these materials contain a hydrophilic substituent and an oleophobic substituent. These substitutions provide the opportunity to structure surfaces which are less susceptible to the formation of adherent films derived from environmental or biological contamination.

Exemplary materials according to the invention include bis(nonafluorohexyl)dichlorosilane, (tridecafluorooctyl)(methoxypolyethyleneoxypropyl)dichlorosilane having 6 to 8 ethyleneoxy units, (tridecafluorooctyl)(methoxypolyethyleneoxypropyl)dimethoxysilane 6 to 8 ethyleneoxy units, bis[methoxy(triethyleneoxy)propyl]dichlorosilane, bis[methoxy(triethyleneoxy)propyl]dimethoxysilane and bis[methoxy(triethyleneoxy)propyl]diethoxysilane. These materials are expected to have utility in surface modification, in particular altering the wettability and release characteristics of siliceous substrates.

The inventive materials may be prepared using a novel multistep synthesis which is also encompassed by the present invention. The method starts with a 1,1,2,2-tetrahydroperfluoroalkyltrichlorosilane or an alkoxypolyethyleneoxyalkyltrichlorosilane. Transformation to the respective hydridodichlorosilane is effected by a hydride transfer reaction. The hydridodichlorosilane is then reacted with the appropriate olefin and may then be converted to an alkoxysilane by well-established esterification procedures.

The innovation of this procedure is what amounts to a step-wise hydrosilylation technique. The partial hydrosilylation of dichlorosilane only proceeds in very low yields. Further, the direct disilylation rarely occurs at all. Without wishing to be bound by theory, it is speculated that the intermediate dichlorosilane interacts with the active platinum (or other) catalyst complex.

The same technique may be applied to the manufacture of bis(perfluoroalkyl)dichlorosilanes and bis[(methoxypolyethyleneoxy)alkyl]dichlorosilanes with >6 EO (ethyleneoxy) units, compounds which are also within the scope of the invention. Such compounds may be described with the formulas (RfCH$_2$CH$_2$)$_2$SiX$_2$ and [R(OCH$_2$CHR')$_m$OR'']$_2$SiX$_2$ Further, [(methoxy(polyethyleneoxy)alkyl]hydridodichlorosilanes are also within the scope of the invention, such as those having the formula [R(OCH$_2$CHR')$_m$OR'']SiHX$_2$. In these formulas, Rf, X, R, R', R'', and m are as previously described.

Siloxanes or silicones may be prepared by hydrolytic condensation of such materials. The hydrolytic condensation may be modified by the presence of end-capping species, such as trimethylchlorosilane, or co-monomers, such as dimethyldichlorosilane, during the hydrolysis. These siloxanes can generally be described as polymers having formula (II):

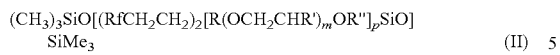

(II)

In formula (II), Rf is a linear or branched perfluorinated hydrocarbon having 4 or more carbon atoms, R is a methyl or ethyl group, R' is H or $CH_3$, m is an integer of 1 to about 24, R" is a hydrocarbon bridge having 1 to about 11 carbon atoms, and p is an integer from 0 to 100.

The invention will now be described in connection with the following non-limiting examples.

EXAMPLE 1

Synthesis of Nonafluorohexyldichlorosilane

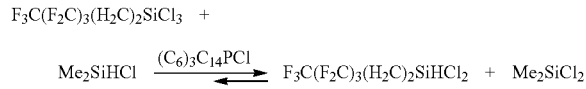

Under a nitrogen atmosphere, a 1-liter 3-necked flask equipped with a heating mantle, magnetic stirrer, pot thermometer, addition funnel and dry-ice condenser was charged with nonafluorohexyltrichlorosilane (457.8 g) and tetradecyl (trihexyl)phosphonium chloride (15.4 g). The mixture was heated to 80° C. and dimethylchlorosilane (124.9 g) was added to the mixture via addition funnel over 1 hr. The pot temperature dropped due to light chlorosilane refluxing. Upon completion of the addition, the reaction was refluxed for 6-8 hrs. The pot temperature slowly increased to 75° C., which indicates the conversion of dimethylchlorosilane to dimethyldichlorosilane. The reaction was cooled to room temperature and GC analysis (low-temp. method) of the mixture indicated about 84% completion. The pot was vented carefully under the protection of nitrogen. Distillation provided 386.6 g of crude product (63.5% pure, 58.0% yield).

EXAMPLE 2

Synthesis of bis(nonafluorohexyl)dichlorosilane

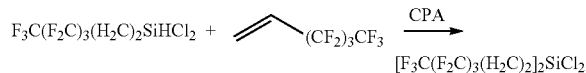

A 1-gallon autoclave was charged with the product of Example 1 (242.9 g), nonafluorohexene (168.81 g), and 5% chloroplatinic acid hexahydrate (CPA) in THF (0.5 mL). The reaction was sealed and heated at 180° C. (PSI ~75) for 24 hrs. The reaction was cooled to room temperature and GC analysis of the mixture indicated completion of the reaction. Purification of the reaction crude by distillation yielded the title compound in 37.1% yield (152.0 g), b.p. 142-148° C./50 mmHg, density @ 20° C. 1.54 g/ml, refractive index @ 20° C.: 1.3440, $^1$H NMR(CDCl$_3$): 1.39 (m, 4H) and 2.30 (m, 4H).

EXAMPLE 3

Synthesis of (tridecafluorooctyl)dichlorosilane

Under a nitrogen atmosphere, a 1-liter 3-necked flask equipped with a heating mantle, magnetic stirrer, pot thermometer, addition funnel and dry-ice condenser was charged with (tridecafluoro-1,1,2,2-tetrahydrooctyl)trichlorosilane (481.6 g) and tetradecyl(trihexyl)phosphonium chloride (12.8 g). The mixture was heated to 85° C. and dimethylchlorosilane (104.1 g) was added slowly to the mixture via the addition funnel over 1-2 hr. After about half of the dimethylchlorosilane had been added, the reaction was cooled to 60° C. and GC analysis indicated 30% conversion. Lights were stripped under full vacuum at room temperature. The reaction was heated at 100° C. and the addition of dimethylchlorosilane was resumed. Upon completion of the addition, the reaction was heated at 75° C. for 1-2 hrs. The reaction was cooled to room temperature and GC analysis of the mixture indicated about 48% completion (started to observe dihydride product). The pot was vented carefully under the protection of nitrogen. Distillation provided 355.3 g of product (53.6 pure, 42.2% yield).

EXAMPLE 4

Synthesis of (tridecafluorooctyl)(methoxypolyethyleneoxypropyl)dichlorosilane (6-8 EO)

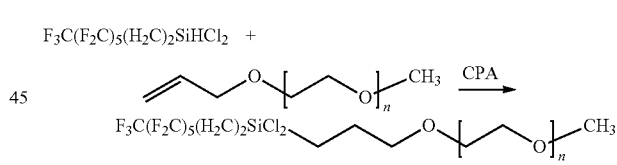

Under a nitrogen atmosphere, a 1-liter 3-necked flask equipped with a heating mantle, magnetic stirrer, pot thermometer, addition funnel and dry-ice condenser was charged with allyloxy(polyethylene oxide)methyl ether (MW ~350, ~6-8 ethylene oxide units) (117.6 g), then heated at 90° C. The product of Example 3 (10 mL) was added through the addition funnel, followed by 5% chloroplatinic acid hexahydrate in THF (0.5 mL). An exothermic reaction was observed immediately and the reaction mixture changed from colorless to dark brown. Once the exotherm was observed, addition of the product from Example 3 was continued through the addition funnel at a rate to maintain the reaction temperature between 90 and 110° C. Upon completion of the addition, an additional 0.25 mL of 5% chloroplatinic acid hexahydrate in THF was added and the reaction was heated at 100° C. for 45 min. The progress of the reaction was monitored by $^1$H NMR. Once the olefin peaks of allyloxy(polyethylene oxide)methyl ether were no longer present, the lights were removed by distillation and the residue from the distillation were carried to the next step without further purification.

EXAMPLE 5

Synthesis of (tridecafluorooctyl)(methoxypolyethyleneoxypropyl)dimethoxysilane (6-8 EO)

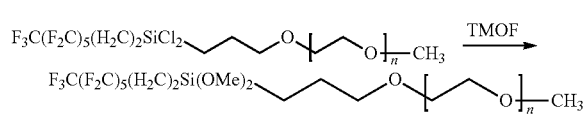

A 2-L flask equipped with magnetic stirring, pot thermometer, addition funnel and a water condenser was charged with the product of Example 4 (334.8 g), then heated to 90-120° C. Trimethyl orthoformate (TMOF) (89.14 g) was added via addition funnel at a rate to control the methyl chloride evolution. Upon completion of the addition, the pH of the reaction mixture was monitored. If the pH of the reaction was acidic, more TMOF was added to complete the reaction. The lights were removed by vacuum distillation. Subsequently, 5 wt % charcoal was added to the residue and the mixture was stirred for 3-4 hrs at 50-60° C. to remove color and yield product in 40.2% yield (132.3 g), density @ 20° C. 1.24 g/ml, refractive index @ 20° C.: 1.3968, $^1$H NMR (CDCl$_3$):0.66 (m, 2H), 0.80 (m, 2H), 1.63 (m, 2H), 2.05 (m, 2H), 3.34 (s, 3H), 3.43 (m, 2H), 3.55 (s, 6H) and 3.56-3.63 (m, 24H).

In order to investigate surface modification, a borosilicate glass slide was immersed in a 5% solution of the title compound in toluene. The slide was air dried and then heated at 110° C. for ten minutes, followed by an ethanol rinse. The dried slides exhibited contact angles of 37° C. with water and 23° C. with hexadecane, respectively.

EXAMPLE 6

Synthesis of Methoxytriethyleneoxypropyldichlorosilane

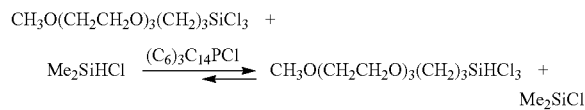

Under a nitrogen atmosphere, a 1-liter 3-necked flask equipped with a heating mantle, magnetic stirrer, pot thermometer, addition funnel and dry-ice condenser was charged with methoxytriethyleneoxypropyltrichlorosilane (339.7 g) and tetradecyl(trihexyl)phosphonium chloride (13.0 g). The mixture was heated to 85° C. and dimethylchlorosilane (104.1 g) was added slowly to the mixture via the addition funnel over 1-2 hrs. After about half of the dimethylchlorosilane had been added, the reaction was cooled to 60° C. and GC analysis indicated 30% conversion. Lights were stripped under full vacuum at room temperature. The reaction was heated at 100° C. and the addition of dimethylchlorosilane was resumed. Upon completion of the addition, the reaction was heated at 75° C. for 1-2 hrs. The reaction was cooled to room temperature and the pot was vented carefully under the protection of nitrogen. Distillation provided 238.4 g of product (60.7% pure, 78% yield, density @ 20° C. 1.013 g/ml).

EXAMPLE 7

Synthesis of bis(methoxytriethyleneoxypropyl)dichlorosilane

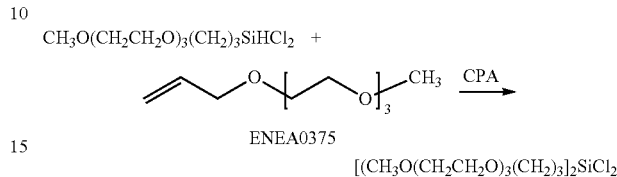

Under a nitrogen atmosphere, a 1-liter 3-necked flask equipped with a heating mantle, magnetic stirrer, pot thermometer, addition funnel and dry-ice condenser was charged with allyloxy(triethylene oxide)methyl ether (76.8 g), then heated at 90° C. The product of Example 6 (10 mL) was added through the addition funnel, followed by 5% chloroplatinic acid hexahydrate in THF (0.5 mL). An exothermic reaction was observed immediately. Once the exotherm was observed, addition of the product from Example 3 was continued through the addition funnel at a rate to maintain the reaction temperature between 90 and 110° C. Additional 5% CPA in THF was added if the temperature dropped below 90° C. Upon completion of the addition, an additional 0.25 mL of 5% chloroplatinic acid hexahydrate in THF was added and the reaction was heated at 100° C. for 45 min. The progress of the reaction was monitored by $^1$H NMR and GC analysis and more allyloxy(triethyleneoxide)methyl ether was added if unreacted product from Example 6 was present. Once the olefin peaks of allyloxy(polyethylene oxide)methyl ether were no longer present, the lights were removed by distillation. The residue from distillation was purified using a Wiped Film Evaporator to afford the desired product in 58.4% yield (139.6 g), 95.0% pure by GC, density @ 20° C. 1.110 g/ml, refractive index @ 20° C.: 1.4618, $^1$H NMR (CDCl3):1.14 (m, 4H), 1.58 (m, 4H), 3.19 (s, 6H), 3.20-3.45 (m, 28H).

EXAMPLE 8

Synthesis of bis(methoxytriethyleneoxypropyl)dimethoxysilane

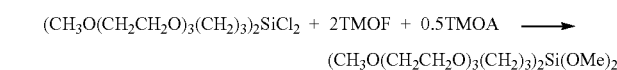

A 1-L flask equipped with magnetic stirring, pot thermometer, addition funnel, vigreux column and distillation head was charged with the product of Example 7 (127.4 g), then heated to 90-120° C. Trimethyl orthoformate (TMOF) (53.06 g) was added via addition funnel at a rate to control methyl chloride evolution. Once the addition of TMOF was completed, the reaction was heated at 140° C. to distill off methylformate. Trimethyl orthoacetate (TMOA) (15.02 g) was added through an addition funnel at a rate to control methyl chloride evolution. Upon completion of the addition, the pH of the reaction mixture was monitored. If the pH of the reaction was acidic, more TMOA was added to complete the reaction. The lights were then removed by vacuum distillation. The product (residue) was obtained in a brown color in 95% yield (125.1 g, density @ 20° C. 1.060 g/ml, refractive index @ 20° C.: 1.4518, $^1$H NMR (CDCl3):0.42 (m, 4H), 1.45 (m, 4H), 3.14 (m, 6H), 3.19 (m, 6H), 3.20-3.45 (m, 28H).

EXAMPLE 9

Synthesis of poly(tridecafluorooctyl)(methoxypolyethyleneoxypropyl)$_{6-8}$ siloxane, trimethylsiloxy terminated

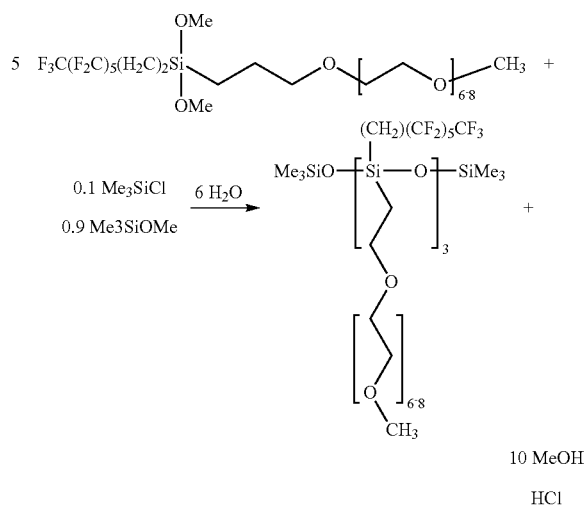

A 100 mL flask equipped with magnetic stirring, pot thermometer, addition funnel and a condenser was charged with a 14 g of (tridecafluorooctyl)(methoxypolyethyleneoxypropyl)$_{6-8}$ dimethoxysilane, 0.04 g of trimethylchlorosilane and 0.33 g of trimethylmethoxysilane. 0.38 g of DI water was added into the above mixture at a pot temperature of 20 to 40° C. After the addition was complete, the reaction mixture was heated at 30 to 50° C. for an additional 90 minutes. Removal of volatiles from the mixture at the pot temperature of 30° C. with ~1 mmHg vacuum yielded 14.7 g viscous liquid: density @ 20° C. 1.450 g/ml, refractive index@ 20°: 1.4047; MW=2000.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A silicon compound having formula (I):

(RfCH$_2$CH$_2$)$_{2-n}$[R(OCH$_2$CHR')$_m$OR"]$_n$SiX$_2$   (I)

wherein Rf is a linear or branched perfluorinated hydrocarbon having 4 or more carbon atoms, R is a methyl or ethyl group, R' is H or CH$_3$, m is an integer of 1 to about 24, R" is a hydrocarbon bridge having 1 to about 11 carbon atoms, n is an integer from 0 to 2, and X is H, Cl or an alkoxy group.

2. The silicon compound according to claim 1, wherein Rf has 4 to about 10 carbon atoms.

3. The silicon compound according to claim 1, wherein m is an integer of about 2 to about 6.

4. The silicon compound according to claim 1, wherein R" is CH$_2$CH$_2$CH$_2$.

5. The silicon compound according to claim 1, wherein X is Cl, OCH$_3$, or OC$_2$H$_5$.

6. A polymeric siloxane compound formed by hydrolytic condensation of the silicon compound according to claim 1.

7. The silicon compound according to claim 1, wherein the compound is a bis[(methoxypolyethyleneoxy)alkyl]dichlorosilane.

8. The silicon compound according to claim 7, having formula [R(OCH$_2$CHR')$_m$OR"]$_2$SiX$_2$.

9. A polymeric siloxane compound formed by hydrolytic condensation of the silicon compound according to claim 7.

10. The silicon compound according to claim 1, wherein the compound is a bis(perfluoroalkyl)dichlorosilane.

11. The silicon compound according to claim 10, having formula (RfCH$_2$CH$_2$)$_2$SiX$_2$.

12. A polymeric siloxane compound formed by hydrolytic condensation of the silicon compound according to claim 10.

13. The silicon compound according to claim 1, wherein the compound is a (tridecafluorooctyl)(methoxypolyethyleneoxypropyl)dichlorosilane.

14. The silicon compound according to claim 1, wherein the compound is a (tridecafluorooctyl)(methoxypolyethyleneoxypropyl)dimethoxysilane having about 6 to 8 ethylene oxide units.

15. The silicon compound according to claim 1, wherein the compound is a bis(methoxytriethyleneoxypropyl)dichlorosilane.

16. The silicon compound according to claim 1, wherein the compound is a bis(methoxytriethyleneoxypropyl) dimethoxysilane.

17. The silicon compound according to claim 1, wherein the compound is a bis(nonafluorohexyl)dichlorosilane.

18. A [(methoxy(polyethyleneoxy)alkyl]hydridodichlorosilane.

19. The silane according to claim 18, having formula [R(OCH$_2$CHR')$_m$OR"]SiHX$_2$, wherein R is a methyl or ethyl group, R' is H or CH$_3$, m is an integer of 1 to about 24, R" is a hydrocarbon bridge having 1 to about 11 carbon atoms, and X is H, Cl or an alkoxy group.

20. The silane according to claim 18, wherein the silane is a methoxytriethyleneoxypropylhydridodichlorosilane.

21. A siloxane polymer having formula (II):

(CH$_3$)$_3$SiO[(RfCH$_2$CH$_2$)$_2$[R(OCH$_2$CHR')$_m$OR"]$_p$SiO]
SiMe$_3$   (II)

wherein Rf is a linear or branched perfluorinated hydrocarbon having 4 or more carbon atoms, R is a methyl or ethyl group, R' is H or CH$_3$, m is an integer of 1 to about 24, R" is a hydrocarbon bridge having 1 to about 11 carbon atoms, and p is an integer from 0 to 100.

* * * * *